United States Patent [19]

Restall

[11] 4,002,183
[45] Jan. 11, 1977

[54] PLAQUE REMOVING DEVICE

[75] Inventor: Raymond B. Restall, Kamloops, Canada

[73] Assignee: The Raymond Lee Organization, Inc., New York, N.Y.; a part interest

[22] Filed: Sept. 8, 1975

[21] Appl. No.: 611,564

[52] U.S. Cl. .................................................. 132/91
[51] Int. Cl.² ........................................ A61C 15/06
[58] Field of Search ...................... 132/89, 91, 92

[56] References Cited

UNITED STATES PATENTS

| 1,512,633 | 10/1924 | Peckham | 132/92 A |
| 2,828,754 | 4/1958 | Stewart | 132/91 |
| 3,927,686 | 12/1975 | Zambito | 132/91 |

*Primary Examiner*—G.E. McNeill
*Attorney, Agent, or Firm*—Daniel Jay Tick

[57] ABSTRACT

A pair of protruding parts extend from one end of an elongated handle in spaced parallel relation. Dental floss is releasably affixed to the protruding parts and extends tautly therebetween.

1 Claim, 5 Drawing Figures

PLAQUE REMOVING DEVICE

DESCRIPTION OF THE INVENTION

The present invention relates to a plaque removing device.

Objects of the invention are to provide a plaque removing device of simple structure, which is inexpensive in manufacture, used with facility and convenience, and functions efficiently, effectively and reliably to meticulously remove plaque from the teeth of a user.

In order that the invention may be readily carried into effect, it will now be described with reference to the accompanying drawing, wherein.

Figure 1:
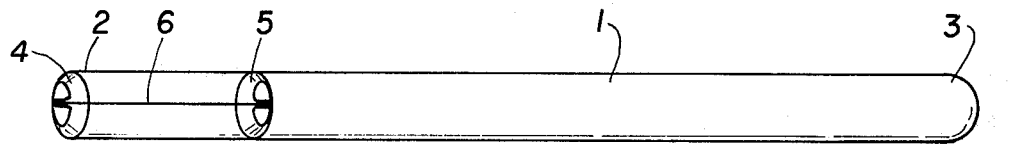
FIG. 1 is a top view of a first embodiment of the device of the invention.

The plaque removing device of the invention comprises a substantially elongated handle 1 having spaced opposite ends 2 and 3. A pair of protruding parts 4 and 5 (FIGS. 1 and 2) or 4' and 5' (FIGS. 3 to 5) extend from the handle 1 at the end 2 thereof in spaced substantially parallel relation.

Dental floss 6 is releasably affixed to the protruding parts 4 and 5 and extends substantially tautly therebetween.

The insertion and removal of the dental floss 6 is facilitated by slots formed in the protruding parts 4 and 5 and 4' and 5', as shown in the FIGS.

Figure 2:
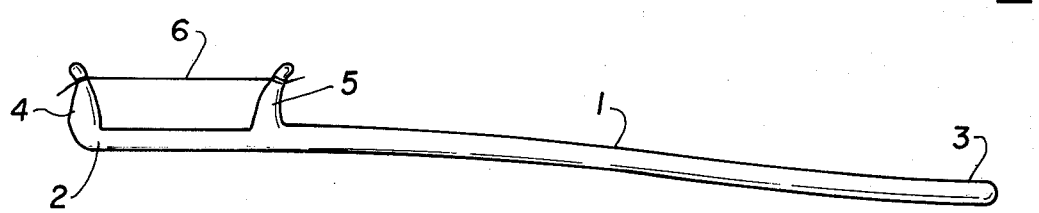
FIG. 2 is a side view, taken along the lines II—II, of FIG. 1.

In the embodiment of FIG. 1, the handle 1 is substantially linear and the protruding parts 4 and 5 are substantially colinear with said handle.

Figure 3:
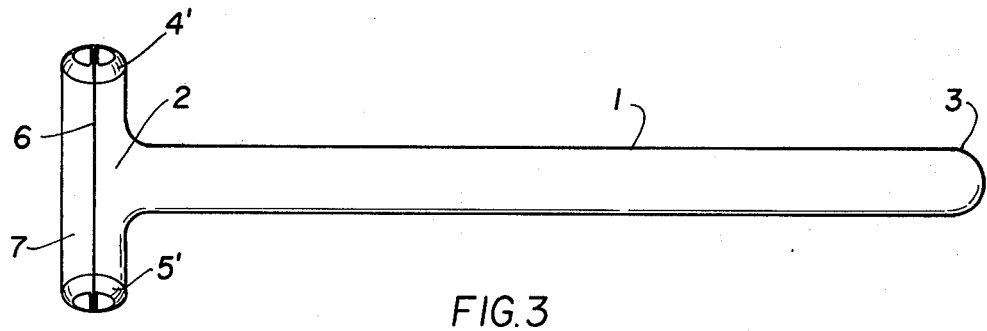
FIG. 3 is a top view of a second embodiment of the device of the invention.
Figure 4:
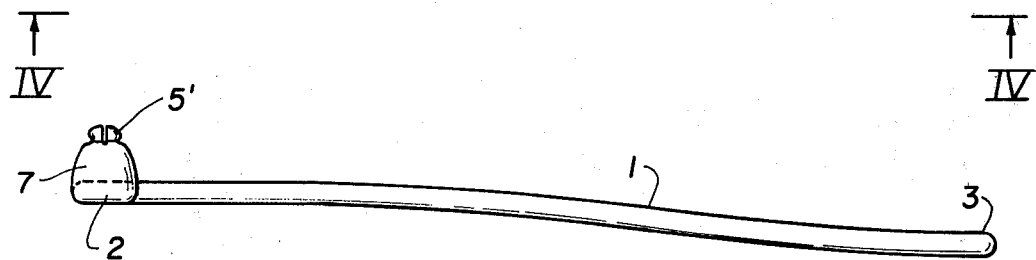
FIG. 4 is a side view, taken along the lines IV—IV, of FIG. 3.

In the embodiment of FIG. 3, the handle 1 has a part 7 extending at substantially right angles to the handle in substantially T-configuration form the end 2 of the handle. The protruding parts 4' and 5' extend from the part 7 substantially colinearly with said part. Thus, the protruding parts 4' and 5' extend from the ends of the part 7.

Figure 5:
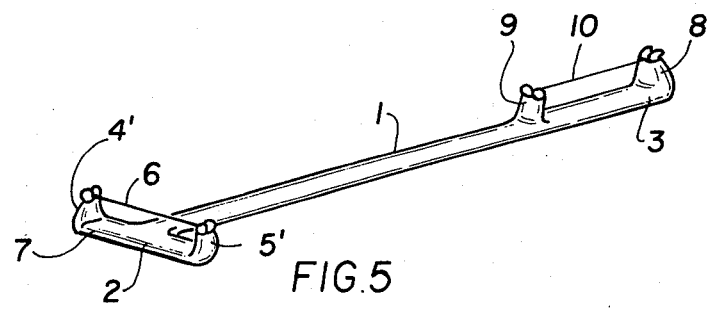
FIG. 5 is a perspective view of a third embodiment of the device of the invention.

In the embodiment of FIG. 5, the handle 1 is substantially linear and a pair of protruding parts 8 and 9 extend from the handle at the end 3 thereof in spaced substantially parallel relation. The remainder of the embodiment of FIG. 5 is the same as the embodiment of FIG. 3. Thus, the handle 1 has a part 7 extending at substantially right angles thereto in substantially T-configuration at the end 2 thereof. A second pair of protruding parts 4' and 5' extend from the part 7 substantially colinearly therewith in spaced substantially parallel relation. The dental floss 6 is releasably affixed to the second pair of protruding parts 4' and 5' and extends substantially tautly therebetween. Dental floss 10 is releasably affixed to the protruding parts 8 and 9 and extends substantially tautly therebetween.

While the invention has been described by means of specific examples and in specific embodiments, I do not wish to be limited thereto, for obvious modifications will occur to those skilled in the art without departing from the spirit and scope of the invention.

I claim:

1. A plaque removing device, comprising
a substantially elongated linear handle having spaced opposite ends, the handle having an arm part extending at substantially right angles thereto in substantially T-configuration from one end thereof and a first pair of protruding parts extending from said arm part substantially colinearly with said arm part, in spaced relation;
a second pair of protruding parts extending from the handle at the other end thereof substantially colinearly therewith in spaced substantially parallel relation, the first and second pairs of protruding parts being substantially parallel to each other; and
dental floss releasably affixed to the first pair of protruding parts and extending substantially tautly therebetween and to the second pair of protruding parts and extending substantially tautly therebetween.

* * * * *